United States Patent [19]
Rabinowitz

[11] Patent Number: 5,096,594
[45] Date of Patent: Mar. 17, 1992

[54] CHROMATOGRAPHIC METHOD OF PURIFYING CYCLITOLS

[76] Inventor: Israel Rabinowitz, 2534 Foothill Rd., Santa Barbara, Calif. 93105

[21] Appl. No.: 634,096

[22] Filed: Dec. 20, 1990

[51] Int. Cl.$^5$ .............................................. B01D 15/08
[52] U.S. Cl. .................... 210/656; 127/46.2; 127/58; 210/198.2; 210/635; 210/638; 210/660; 568/833; 568/872
[58] Field of Search ............... 210/660, 666, 667, 669, 210/679, 656, 198.2, 635, 638; 436/161, 178; 568/872, 833, 917; 560/157; 435/84; 73/61.1 C; 127/46.2, 55, 46.2, 58

[56] References Cited

U.S. PATENT DOCUMENTS

| | | | |
|---|---|---|---|
| 2,615,053 | 10/1952 | Artz et al. | 568/872 |
| 4,066,711 | 1/1978 | Melaja et al. | 568/872 |
| 4,456,774 | 6/1984 | Sherman et al. | 568/872 |
| 4,482,761 | 11/1984 | Chao et al. | 568/872 |
| 4,544,778 | 10/1985 | Chao et al. | 127/46.2 |
| 4,631,129 | 12/1986 | Heikkila | 210/659 |
| 4,946,779 | 8/1990 | Kameda et al. | 435/84 |

OTHER PUBLICATIONS

O. Samuelson, "Ion Exchange", vol. 2, J. Marinsky Editor, Dekker, New York, 1969, pp. 167-177.
O. Mikes and R. Vespalec, "Liquid Column Chromatography", vol. 3, Z. Deyl, K. Macke & J. Janaka, editors, Elsevier, Amsterdam, pp. 261-262, 269.
L. R. Snyder and J. J. Kirkland, "Introduction to Modern Liquid Chromatography", 2nd ed., Wiley, New York, pp. 246-251, 410-411, 426-427, 446-447.
S. Budavari, editor, "The Merck Index", 11th ed., Merck & Co., Inc., Rahway, N.J., U.S.A., 1989, p. 788.
R. C. Bennett, Chem. Eng. Progress Symp. Series, 65, No. 95, p. 34 (1969), J. A. Palermo and M. A. Lason, ed.
M. L. Greenburg, B. Reiner, and S. A. Henry, Genetics, 100, 19 (1982).
B. J. Holub, Ann. Rev. Nutr., 6, 563 (1986).
M. J. Jackson & S. Shin, Cold Spring Harbor Conf. Cell Proliferation, 9, 75 (1982).
W. L. McCabe and J. C. Smith, Unit Operations of Chem. Eng., 3rd ed., McGraw Hill, New York (1976).

*Primary Examiner*—Robert A. Dawson
*Assistant Examiner*—Sun Uk Kim
*Attorney, Agent, or Firm*—David J. Larwood

[57] ABSTRACT

A method of purifying cyclitols, particularly inositol, from mixtures including simple and complex carbohydrates begins by reducing the concentration of carbohydates other than cyclitols to facilitate separation and crystallization of the cyclitol in high purity. This separation can be achieved by separating carbohydrates on a chromatographic column then concentrating and crystallizing cyclitol from selected fractions.

11 Claims, 1 Drawing Sheet

CHROMATOGRAPHIC METHOD OF PURIFYING CYCLITOLS

FIELD OF THE INVENTION

A method is described which allows simple separation of cyclitols and alditols from mono- and disaccharides. This is particularly useful in purifying cyclitols and alditol from plant sources, including corn steep liquor and almond hull juice.

BACKGROUND OF THE INVENTION

Cyclitols such as inositol are found in nature in a large number of plants. Inositol has been identified as a valuable nutrient and was for some time classified as one of the B-vitamins. Inositol was fist claimed to have vitamin activity by D.W. Woolley, primarily due to its antialopecia effect in mice. M. J. Jackson, S. Shin, *Cold Spring Harbor Conf. Cell Proliferation*, 9, 75 (1982). Classification as a vitamin was however confused for some time due to difficulties in analytical techniques for inositol and the successive finding of great variability in endogenous synthesis of inositol in different animals and different tissue types within these animals.

Inositol is not now considered a true vitamin for humans, although it is clear that is essential for the survival and growth of many human cell types. *ibid.* Animals, including humans, normally synthesize endogenous inositol, but inositol deficiency can exist in animals which can lead to disease conditions. B. J. Holub, *Ann. rev. Nutr.*, 6, 563 (1986). Recognizing the importance of inositol in animals, especially during periods of rapid growth, the U.S. Food and Drug Administration has set a requirement for inclusion of inositol in infant formulas which do not contain milk (a good source of inositol). 21 C.F.R. 107.100 (1987).

In yeast, and possibly higher animals, inositol appears to play some essential role in membrane phospholipid balande, and is required for proper growth. See Greenberg et al., *Genetics*, 100:19-3 (Jan. 1982). The standard commercial source for inositol is corn steep liquor since inositol is present as phytic acid in corn. See Artz, et al., U.S. Pat. No. 2,615,053, and The Merck Index, compound 4823 page 788, Merck & Co., 11th Ed. (1989).

Traditionally, inositol or cyclitols have been separated from a mixture of alditols and sugars, both simple and complex. Inositol has been purified by selective adsorption on zeolite molecular sieves. Chao, U.S. Pat. No. 4,482,761. Cyclitols can be crystallized from a mixture of sugars, but such crystaliizations typically include and occlude a significant number of impurities. Another traditional method of purification is to pass a mixture of sugars, alditols and cyclitols through an appropriate column to separate cyclitols from other sugars before crystallization.

SUMMARY OF INVENTION

The present invention describes a method of selectively removing sugars from a mixture of sugars and sugar alcohols. The present invention also includes a method for removing alditols from the cyclitols, further simplifying purification of cyclitols. The feed stock for this invention can be any of a number of plant juices, including corn steep liquor, almond hull juice, cane and beet sugar molasses, sorghum molasses, wood molasses, and various fruit juices including cherry, plum (prune), pineapple, citrus, apple, etc.

Plant juice extracts were purified by column chromatography using DMSO:water gradients. The resulting fractions were concentrated, then cyclitols were crystallized in high yield and high purity.

One object of this invention is to provide a solution of cyclitol relatively free of mono- or polysaccharides.

Another object of this invention is to provide highly purified, crystalline cyclitol.

DETAILED DESCRIPTION

Figure 1:
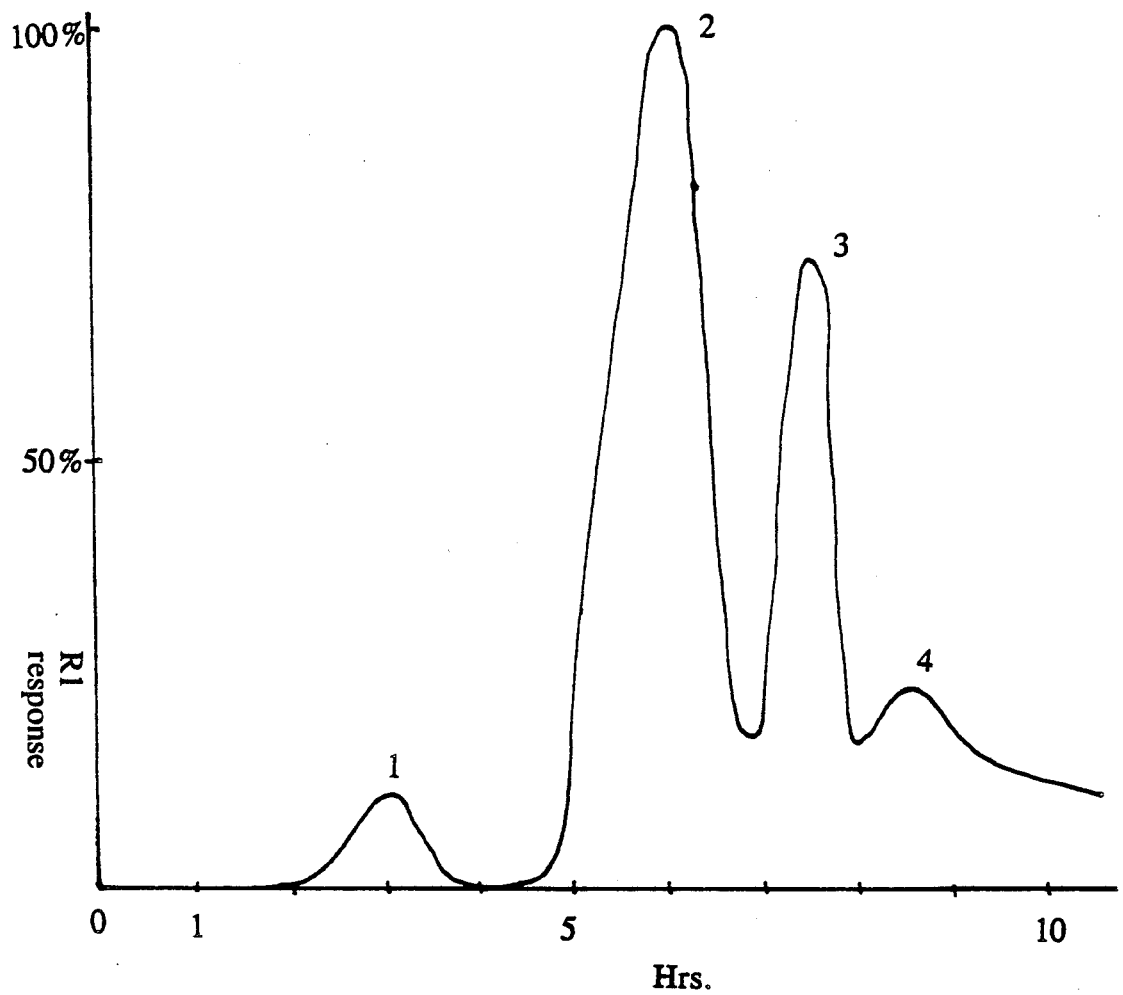
FIG. 1 illustrates a chromatographic separation of various sugars on a cation exchange resin in the lead counter-ion form.

Inositol was separated from other carbohydrates in plant juice extracts. One suitable plant juice is almond hull juice, prepared by leaching almond hulls with hot water. A 30° Brix solution of almond hull juice (AHJ) has roughly 1.75.0 g/l of fermentable sugars, mostly glucose, fructose and sucrose. Other suitable plant juices include, for example, corn steep liquor, cane and beet sugar molasses, sorghum molasses, wood molasses, and various fruit juices including cherry, plum (prune), pineapple, citrus, apple, etc. Juices can be prepared by leaching the plant material using a suitable solvent, usually hot water. See W. L. McCabe and J. C. Smith, *Unit Operations of Chemical Engineering*, Third Edition, McGraw Hill, New York (1976). The specific leaching process and its operating conditions would in general depend on the plant material employed, as is well understood by persons skilled in the art.

The selected plant juice was concentrated above 6° Brix, then applied to a column as described below. Solvent was partially removed from selected fractions, and inositol was crystallized. Mixtures of inositol and sorbitol could be selectively crystallized to provide crystalline inositol and a concentrated syrup of sorbitol, suitable for crystallization and further purification.

Purification of Inositol by Chromatography

Commercially available ion exchange resin, a cation exchange styrene-divinylbenzene with sulfonic acid derivitization was used for pilot scale separations of inositol from other sugars and cyclitols in almond hull juice extract.

The column used was water jacketed with a resin bed of approximately 145 cm. × 2.5 cm. 30° C.–60° C. Brix syrup extracts of almond hulls were run through the column at 60° C.–80° C. in plug flow mode. The resin was used in both the calcium counter ion form and the lead counter ion form. Elution solvent was dimethylsulfoxide (DMSO):water in ratios of 2.5:97.5 to 30:70 v/v.

With the resin in the calcium form, inositol eluted from the column imperfectly separated from fructose, i.e. there was no "peak to peak" separation. However, we discovered that inositol has a lower solubility in DMSO:water solutions that in water alone whereas fructose, glucose and sucrose retain the high solubilities. Using the cation exchange resin in either the calcium or lead counter-ion form, the critical separation is that of fructose from inositol, as these two compounds elute together, or with poor separation, using conventional process variables. Table 1 shows the solubilities of inositol can be fractionally recrystallized from a fructose-inositol solution in DMSO:water with fructose concentration as high as 30% w/v. Table 1 also indicates that inositol crystallization yields are higher upon cooling a DMSO:water solution compared to cooling a hot aqueous solution.

For the measurements summarized in Table 1, reagent grade fructose and inositol were obtained from Sigma Chemical Co. Technical grade DMSO obtained from Gaylord Chemical Co. Standard volumetric glassware was used to measure volumes, and analystical balance used to weight sugars and dry crystal yields. Crystals were separated from suspension by centrifugation at approximately 2,000×g for 30 minutes, then dried at 90° C. for 24 hours prior to weighing.

Crystallization Theory

The crystallization process from a solution involves the initial nucleation of the material to be crystallized, its growth to this final size, or crystal size distribution, and recovery from solution. Since the first recorded sugar crystallizations from solution, ca. 500 A.D., efforts have been made to (1) control the nucleation step, which in turn lead to a narrower crystal size distribution, (2) improve product yield and (3) improve product purity. R. C. Bennett, *Chem. Eng. Progress Symp. Series*, 65 (95), 34 (1969).

TABLE 1

Dissolution and Recrystallization of Inositol and Fructose in Water and DMSO:Water Solutions

| Percent Inositol or Fructose (W/V) | 10 | 12 | 15 | 17 | 20 | 22 | 25 | 30 |
|---|---|---|---|---|---|---|---|---|
| Percent Dissolution of Inositol in Cold Water | 100 | 100 | 99[1] | — | 85 | — | — | — |
| Percent Dissolution of Inositol in Hot (95° C.) Water | 100 | 100 | 100 | 100 | 100 | 100 | 100 | 100 |
| Percent Dissolution of Fructose in Hot Water (95° C.) and Cold (25° C.) Water | 100 | 100 | 100 | 100 | 100 | 100 | 100 | 100 |
| Percent Dissolution of Inositol in 15% DMSO:Water (V/V) Cold (25° C.) | — | — | 60 | — | 50 | — | — | — |
| Percent Dissolution of Inositol in 15% DMSO:85% Water (V/V) Hot (95° C.) | 100 | 100 | 100 | 100 | 100 | 100 | 100 | 100 |
| Percent Dissolution of Fructose in 15% DMSO:85% Water (V/V) Cold (25° C.) | 100 | 100 | 100 | 100 | 100 | 100 | 100 | 100 |
| Percent Dissolution of Fructose in 15% DMSO:85% Water (V/V) Hot (95° C.) | 100 | 100 | 100 | 100 | 100 | 100 | 100 | 100 |
| Percent Recrystallization of Inositol on Cooling Hot Water Solution to 25° C. | 0 | 0 | 0 | 5 | 10 | 15 | 20 | 50 |
| Percent Recrystallization of Inositol on Cooling Hot DMSO:Water Solution to 25° C. | 5 | 20 | 30 | 60 | 80 | 90 | 95 | — |
| Percent Recrystallization of Fructose on Cooling Hot Water Solution to 25° C. | 0 | 0 | 0 | 0 | 0 | 0 | 0 | 0 |
| Percent Recrystallization of Fructose on Cooling Hot DMSO:Water Solution to 25° C. | 0 | 0 | 0 | 0 | 0 | 0 | 0 | 0 |

[1]Solubility of inositol at 25° C. is 14 g/100 ml. Merck Index, loc. cit

With the resin in the lead form, changing DMSO:water ratios isocratically from near 2.5:97.5 t 30:70 resulted in increasing the peak to peak separation of inositol from fructose. The other sugars, as in the case of the calcium form, separated as pure fractions prior to the elution of fructose or inositol. The result of a one separation is shown in FIG. 1. This shows a separation on a Spectrum Corp. Spectra-Chrom glass column, water jacketed, 2.5 cm I.D. ×180 cm. Resin heights during operation averaged 145–160 cm. Runs were performed at 65° C. over styrene divinylbenzene cation exchange resin TCC-14M, obtained from TechniChem, inc., Belvedere, Ill. FIG. 1 is the result of a run in lead counterion form. A 4.7 ml sample of 50.4° Brix almond hull syrup (previously ultrafiltered and deionized) was applied to the column. Elution at 4 ml/min was controlled by a Cole-Parmer variable speed Masterflex peristaltic pump using silicone tubing and an elution solvent of DMSO:$H_2O$, 10:90 v/v. The column output was taken through a Knauer Model 198 refractive index detector to a Spectrum Corp. Chrom Fraction Collector. Peak 1 is sucrose, peak 2 is glucose, peak 3 is fructose and peak 4 is inositol. Sorbitol eluted later and is not shown.

The chemical composition of the solution from which a compound is to be crystallized affects nucleation kinetics as well as crystal morphology ("shape"), which has significant practical and commercial implications. The chemical composition of the solution will also contribute to impurity problems of the crystal product either as crystal inclusion impurity or absorbed impurities on the crystal surface. The chemical composition of the solution will affect product yield either by decreasing the practical degree of supersaturation attainable prior to nucleation (cf: below), or by necessitating additional recrystallization steps to purify the product.

The first step in the crystallization process is reaching the optimum supersaturation point for the compound in solution. Inositol has a marked temperature dependent solubility. Crystallizing inositol from a solution of inositol in water should be, and is, a straightforward procedure of concentration of inositol in water at an elevated temperature, via evaporation, or some other mean of water removal, followed by temperature reduction to initiate nucleation, with or without the introduction of "seed" crystals.

The sugar alcohol inositol, as found in almond hull juice extract, is in the presence of mono and disaccharides, namely glucose, fructose, sucrose, and sorbitol. The ratio of the sugars to inositol is approximately 8–10:1. Concentration of inositol in almond hull extract to the supersaturation point is best preceded by an inositol "enrichment" step: i.e. the concentration of inositol should be increased relative tot he concentration of other sugars and sugar-like components. This can be accomplished via a chromatographic separation.

Concentrating inositol along with concentrating the other sugars would result in severe viscosity problems affecting nucleation and crystal growth, and potentially severe contamination of the inositol crystals by adsorption or inclusion of other sugars. Furthermore, yield per each batch crystallization step would be reduced due to viscosity and contaminant interference with achieving a high "$\Delta C$," where $$\Delta C = C_{supersat.} - C_{sat.}$$

i.e. the concentration of supersaturated inositol minus concentration of saturated inositol. This terminology is not equivalent to the accepted definition of supersaturation $$P = C_{super} - C_{sat.} \text{(constant temp)}$$

which refers to the concentration of a material at supersaturation point, minus concentration at saturation point, at the same temperature. The "$\Delta C$" referred to above is meant to emphasize the high supersaturation of inositol which can be achieved by exploiting the temperature dependent concentration properties of inositol. Stated in another way, perhaps, inositol can be supersaturated into the labile supersaturated region, where seed nucleation is not necessary, rather than the metastable supersaturation region, where seeding is necessary for nucleation.

Crystallization Method

Eluted fractions of pure inositol, for example the inositol peak shown in FIG. 1, or inositol-fructose fractions from runs on a calcium counter-ion exchange resin, were collected in a fraction collector or manually into flasks. Test tube volumes were typically 10 ml, with fractions of interest in 7 to 20 tubes. Dilution factors for inositol concentrations were therefore at least seven fold; e.g. a plug injection of 5.0–10.0 ml of 50° Brix extract syrup containing 5–10% inositol would yield a pure inositol fraction with a concentration of about 0.3–1.4%. Aliquots of pure inositol fractions were evaporated at 80–90° C. down to final volumes in which inositol exceeded the solubility limit at 25° C. The final evaporated volumes were maintained at 5–10° C. overnight for nucleation and growth of crystals. Experiments with samples of almond hull syrup spiked with pure inositol to just below saturation at 65°) C. (approximately 0.45 g/ml) allowed more accurate recovery and weighing of crystallized inositol. Recovery percentages for inositol were in the range of 50–60%. Crystals were well-formed parallelopipeds characteristic of the monoclinic crystal class of inositol. Melting points fell within the 223–226° C. range for anhydrous myo-inositol. (Mel-Temp II. Laboratory Devices, Holliston MA). Purity of the crystals was 90%, as determined by microbiological assay (Hazelton Laboratories, Madison WI). The crystals were not washed with cold water or recrystallized prior to microbiological assay.

The use of a mixture of DMSO:water as an elution solvent has three advantages. The first is that DMSO added to the water increases resolution when separating inositol from other sugars and cyclitols, even though in the case of calcium counter ion resin, this resolution is not complete, in our hands. The second advantage is that DMSO:water solutions increase the solubility difference between inositol and the other sugars, allowing easier fractional crystallization of inositol in the presence of other sugar. Further, whereas the solubility of inositol in hot DMSO approaches that of inositol in hot water, the solubility of inositol in cold DMSO is much less than inositol in cold water. This allows greater yields of inositol crystals per batch or semi-batch crystallization by cooling. The third advantage makes use of the solvent properties of DMSO for aromatic hydrocarbons. What we have observed is that the aromatic polyphenolic fraction ("tannin") which is present in solution with the sugars and cyclitols, elutes just prior to the sugars and inositol. Thus, much of the color molecules of the syrup, as well as other organic molecules which inhibit nucleation and crystal growth, are removed prior to collection of the inositol fraction.

What is claimed is:

1. A method of purifying cyclitols from a mixture of carbohydrates by passing the mixture through a chromatographic column comprising preparing an ion exchange column in a suitable salt form, applying a plant juice mixture, then eluting with a DMSO:water gradient.

2. The method of claim 1 wherein said plant juice is almond hull juice.

3. The method of claim 2 wherein said almond hull juice has a concentration of more than 6° Brix.

4. The method of claim 3 wherein said almond hull juice has a concentration of more than about 30° Brix.

5. The method of claim 1 wherein said cyclitols include inositol.

6. The method of claim 1 wherein the eluant from said column is concentrated and said cyclitols are crystallized from a mixture of DMSO and water.

7. The method of claim 6 wherein said cyclitols include inositol.

8. The method of claim 1 wherein said ion exchange column comprises a cation exchange styrene-divinylbenzene with sulfonic acid derivitization.

9. The method of claim 1 wherein said ion exchange column is in the calcium counter ion form.

10. The method of claim 1 wherein said ion exchange column is in the lead counter ion form.

11. The method of claim 1 wherein said DMSO:water composition varies between approximately 2.5:97.5 and approximately 30:70 v/v.

* * * * *

UNITED STATES PATENT AND TRADEMARK OFFICE
CERTIFICATE OF CORRECTION

PATENT NO. : 5,096,594
DATED      : Mar. 17, 1992
INVENTOR(S): Israel Rabinowitz It is certified that error appears in the above-identified patent and that said Letters Patent is hereby corrected as shown below:

In column 1, line 40, change "balande" to read --balance--.

In column 1, line 45, change "4823page" to read --4823 page--.

In column 2, line 33, change "above 6°" to read --above about 6°--.

In column 2, line 48, change "30°C.-60°C." to read --30°-60°--.

In column 3, line 47, change "t" to read --to--.

In column 5, line 8, change "tot he" to read --to the--.

Signed and Sealed this

Twenty-eighth Day of September, 1993

Attest:

BRUCE LEHMAN

*Attesting Officer*     *Commissioner of Patents and Trademarks*